(12) United States Patent
Adkins

(10) Patent No.: US 6,384,362 B1
(45) Date of Patent: May 7, 2002

(54) METHOD AND APPARATUS FOR DESTROYING NEEDLES

(76) Inventor: Joey B. Adkins, 6058 Millwood Dr., Broadview Heights, OH (US) 44147

( * ) Notice: Subject to any disclaimer, the term of this patent is extended or adjusted under 35 U.S.C. 154(b) by 0 days.

(21) Appl. No.: 09/500,504

(22) Filed: Feb. 9, 2000

(51) Int. Cl.$^7$ .............................. B23H 1/00; B23K 9/00
(52) U.S. Cl. ........................................ 219/68; 219/69.1
(58) Field of Search ................................... 219/68, 69.1

(56) References Cited

U.S. PATENT DOCUMENTS

| | | |
|---|---|---|
| 3,392,255 A | 7/1968 | Rye et al. |
| 3,401,723 A | 9/1968 | Petry |
| 3,429,743 A | 2/1969 | Branson |
| 4,538,043 A | 8/1985 | Alexander |
| 4,628,169 A | 12/1986 | Ch'ing-Lung |
| 4,877,934 A * | 10/1989 | Spinello ...................... 219/68 |
| 4,961,541 A | 10/1990 | Hashimoto |
| 4,965,426 A | 10/1990 | Colombo |
| 5,076,178 A * | 12/1991 | Kohl et al. .................. 110/250 |
| 5,091,621 A | 2/1992 | Butler |
| 5,138,124 A | 8/1992 | Kirk et al. |
| 5,138,125 A | 8/1992 | Salesses |
| 5,166,488 A | 11/1992 | Peppard |
| 5,212,362 A * | 5/1993 | Burden et al. ............. 219/69.1 |
| 5,245,935 A | 9/1993 | Fukuda |
| 5,264,675 A | 11/1993 | Butler |
| 5,268,549 A | 12/1993 | Butler |
| 5,276,297 A | 1/1994 | Nara |
| 5,282,428 A | 2/1994 | Grenville et al. |
| 5,288,964 A | 2/1994 | Walker et al. |
| 5,294,767 A * | 3/1994 | Cantarero ...................... 219/68 |
| 5,300,752 A | 4/1994 | Elmerick et al. |
| 5,329,087 A | 7/1994 | Kohl et al. |
| 5,334,812 A | 8/1994 | Hsieh |
| 5,336,862 A * | 8/1994 | Yelvington .................... 219/68 |
| 5,365,029 A * | 11/1994 | Makihara ...................... 219/68 |
| 5,391,849 A | 2/1995 | Furuya et al. |
| 5,468,928 A * | 11/1995 | Yelvington .................... 219/68 |
| 5,525,772 A | 6/1996 | Tanguy |
| 5,540,416 A | 7/1996 | Huang |
| 5,545,869 A | 8/1996 | Piva |
| 5,548,095 A | 8/1996 | Cornell |
| 5,551,355 A | 9/1996 | Haines et al. |
| 5,637,238 A | 6/1997 | Truesdale et al. |
| 5,676,859 A | 10/1997 | Yanobu |
| 5,710,404 A | 1/1998 | Descent |
| 5,736,706 A * | 4/1998 | Butler ......................... 219/68 |
| 5,741,230 A | 4/1998 | Miller |
| 5,765,490 A | 6/1998 | Colin et al. |
| 6,169,259 B1 * | 1/2001 | Hall et al. ..................... 219/68 |

FOREIGN PATENT DOCUMENTS

| | | | | |
|---|---|---|---|---|
| GB | 2268407 | * | 1/1994 | ................... 219/68 |
| GB | 2297230 | * | 7/1996 | ................... 219/68 |
| WO | WO-97/33639 | * | 9/1997 | ................... 219/68 |

* cited by examiner

Primary Examiner—Tom Dunn
Assistant Examiner—L. Edmondson
(74) Attorney, Agent, or Firm—Lightbody Law Office

(57) ABSTRACT

Biohazardous needles are destroyed by the application of an electrical arc that progressively destroys the needle and seals hollow needles. An elongate electrode that slopes up and away from the needle supports is used to strike an then progressively support the destructive arc.

16 Claims, 1 Drawing Sheet

METHOD AND APPARATUS FOR DESTROYING NEEDLES

BACKGROUND OF THE INVENTION

This invention relates to the destruction of biohazardous needles and, in particular, to the electrical destruction of used hypodermic needles.

Increasing emphasis has been placed on protecting patients and health professionals from needle sticks that may spread such pathogens as hepatitis and HIV. Various disposal containers have been used. Needles with various shielding schemes have been employed. Devices that cut needles have been tried.

To destroy the needle itself, devices have been used that melt the needle by connecting the needle across a large current source. Such devices require an extreme amount of current because of the relatively low resistance of the needle. This makes portable use impractical and line-powered power supplies expensive. In addition, this destruction mechanism soon destroys the contacts of the device as well as the needles.

SUMMARY OF THE INVENTION

An apparatus for destroying a biohazardous needle having a proximal portion and a distal tip portion includes: an upper electrode adapted to contact the proximal portion; a lower electrode; and an electric arc supply connectable between the upper and lower electrodes. The supply is adapted to produce an electric arc between the lower electrode and the distal tip portion to destroy the needle.

A method for destroying a biohazardous needle having a proximal portion and a distal tip portion includes: providing an electric arc supply having an upper and a lower output contact; connecting the upper output contact to the proximal portion; and creating an arc between the distal tip portion and the lower output contact where the arc progressively destroys the needle.

DESCRIPTION OF THE PREFERRED EMBODIMENTS

Figure 1:
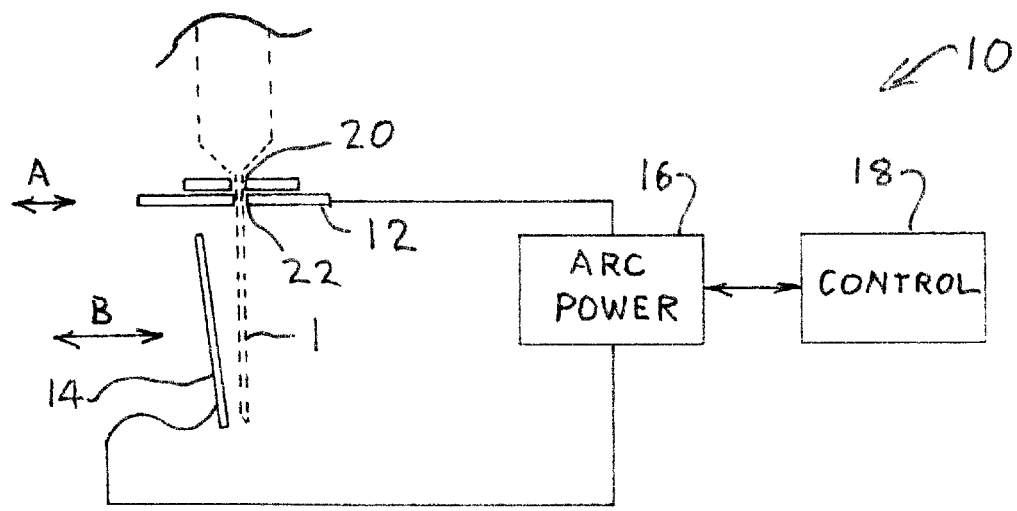
FIG. 1 is a schematic diagram of a needle destroying apparatus according to the invention.

Referring to FIG. 1, a needle destroying apparatus 10 includes an upper electrode 12, a lower electrode 14, an arc power supply 16 and a control 18.

The needle 1 may be advantageously immobilized by a shutter effect between a stationary aperture 20 and an aperture 22 in the plate-like electrode 12 when the electrode 12 is moved along the direction A. The electrode 12 may be moved by various mechanisms, including, for example, a manually operated linkage or camming action or such other well-known techniques as an electrically-operated solenoid or motor and gear train or linkage. The upper electrode may be, for example, comprised of stainless steel. It would of course be possible to maintain the electrode 12 stationary and instead move the aperture 20 (i.e., a member containing the aperture 20)

The electrode 14 may advantageously be an elongate member lying generally in a plane through the needle 1. The lower portion of the electrode 14 is located closer to the tip or distal portion of the needle 1 than is the upper portion of the electrode 14 with respect to the upper or proximal portion of the needle 1. In the preferred embodiment, the electrode 14 is a straight rod of a heat-resistant electrical conductor. The electrode may be, for example, stainless steel, or for higher heat resistance, tungsten. The electrode 14 may be, for example, a circular rod as long or longer than the needle to be destroyed and between 0.020 and 0.060 inches in diameter, with 0.032 inches preferred.

The electrode 14 may be mounted on a carrier more fully described below. The electrode 14 may be moved along the direction B by various mechanisms, including, for example, a manually operated linkage or camming action or such other well-known techniques as an electrically-operated solenoid or motor and gear train or linkage. As more fully described below, movement of the electrode along the direction B facilitates the striking of an electric arc between the electrode 14 and the needle 1, as well as the removal of "ash" from the end of the needle 1.

The arc power supply 16 provides high voltage between the electrodes 12, 14 sufficient to establish an air arc between the needle 1 and the electrode 14 while the proximal portion of the needle 1 is in electrical contact with the electrode 12. The arc supply 16 provides sufficient current in combination with the voltage to destroy the needle 1 using the heat of the arc to a point close to the electrode 12.

The arc supply 16 may include, for example, a battery or line powered oscillator driving a step-up transformer. The output of the arc supply may be, for example, about 25 milliamps at 800 volts for needles in the range of 27–32 gauge. Larger needles of 18–26 gauge may require about 125 milliamps at 800 volts. In general, a maximum arc distance of about one-quarter inch has been satisfactory. In the preferred embodiment, the arc supply 16 includes a full-wave rectifier that provides direct current to the electrodes 12, 14 with the electrode 12 having a negative polarity with respect to the electrode 14.

The control 18 controls the operation of the apparatus 10. The control 18 may be, for example, simply a manual switch to control power to the arc supply 16 or it may be a more complex device as described more fully below.

In operation, the needle 1 of a syringe or other biohazardous needle is inserted into the aperture 20. The electrode 12 is moved to contact the needle 1 trapping it between the walls of the aperture 20 and the aperture 22. The arc supply 18 is energized and the electrode 14 moved against the distal tip of the needle 1, temporarily shorting the arc supply 18, and the electrode 14 is then pulled away from the needle 1 thereby striking an arc between the needle 1 and the electrode 14. The resulting arc melts/burns the tip of the needle 1 and the arc continues up the portion of the electrode 14 closest to the remaining lower portion of the needle 1, progressively destroying the needle as the arc travels upward.

After the needle 1 is destroyed by the arc, the electrode 12 is released and the stub of the needle 1 withdrawn from the apertures 20, 22.

The increasing distance between the electrode 14 and the needle 1 towards the upper proximal portion of the needle 1 helps ensure that the arc starts at the distal tip of the needle 1 and moves toward the proximal portion. This is due to a combination of air heated by the arc tending to push the arc upward balanced by the tendency for the arc to jump to the closest point between the electrode 14 and the needle 1. The needle/electrode are not required to be in a vertical plane but the proximal portion of the needle 1 should be higher than the distal tip. The angle between the needle 1 and the electrode 14 may be, for example, between 10 and 15 degrees with 12 degrees being satisfactory.

In the case of hollow hypodermic needles, the apparatus 10 has the further advantage that the progressive melting of the needle 1 results in a melted bead of metal that both blunts and seals any remaining portion of the needle 1.

By maintaining the electrode 12 negative with respect to the electrode 14, it has been found that the majority of the heat from the arc is transferred to the needle 1 instead of to the electrode 14, greatly improving the durability of the electrode 14.

It has been found that the use of an air arc to destroy the needle, as opposed to destroying it with a short circuit, requires much less power and greatly improves the durability of the contact electrodes. The lower power required makes it possible to operate the device for small gauge needles such as insulin syringes on a few AA batteries for hundreds of needles. In this low power configuration, it is desirable to move the electrodes 12, 14 with a manually operated linkage that also operates a switch for the control 18.

Figure 2:
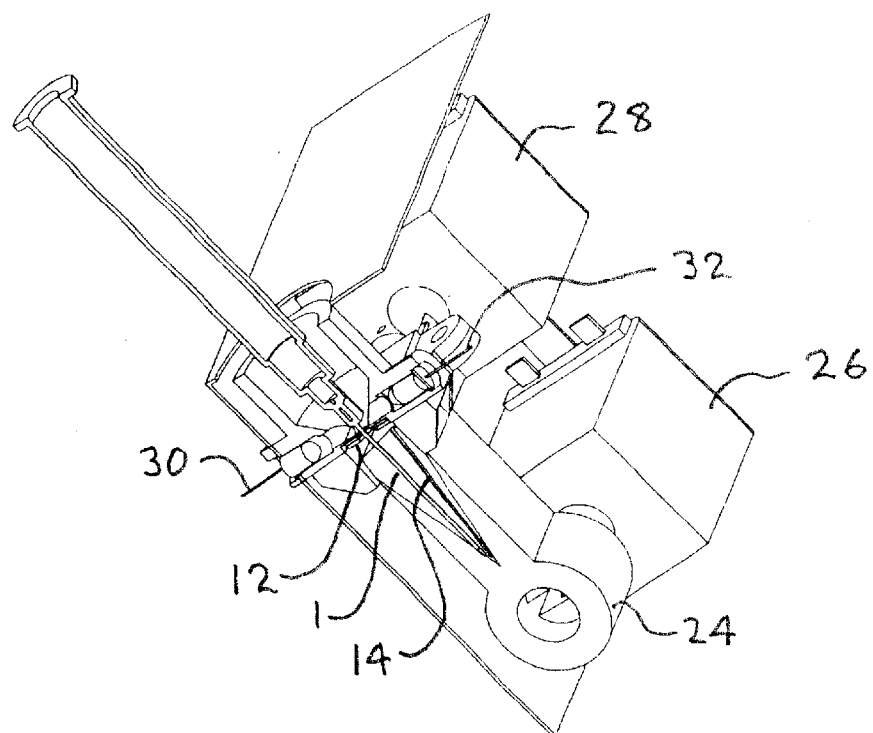
FIG. 2 is a perspective view with portions cut away of an apparatus according to the invention.

Referring to FIG. 2 a solenoid-based embodiment of the invention includes a carriage 24 carrying the electrode 14 at the bottom of a v-shaped groove. The carriage 24 may be, for example, an electrically insulating plastic or, for higher heat resistance, a ceramic material. The carriage 24 is mounted on the plunger of a solenoid 26 and the electrode 12 is mounted to the plunger of a solenoid 28. A light emitting diode 30 and a phototransistor 32 are mounted about the needle 1.

In this case, the control 18 uses the diode 30 and the transistor 32 to detect the presence of a needle 1. The control 18 energizes the solenoid 28 to move the electrode 12 to contact and grasp the needle 1. The control 18 also energizes the solenoid 26 to bring the electrode 14 into momentary contact with the needle 1 to strike the arc.

When operating with larger gauge needles, ash may be left in place of portions of the needle 1 resulting in interference with the progression of the arc. The solenoid 26 may also be energized by the control 18 to use the carriage 24 to periodically knock this ash loose.

For longer needle lengths, the electrode 14 can be advantageously increased in length also. This results in an electrode having an upper portion that would be much farther away from the needle 1 when the lower portion of the needle was in contact with or close to the distal tip of the long needle. This would then require a much higher voltage to sustain the arc at the proximal portion of the needle 1. This would in turn negatively impact the required power, the dissipated heat and the required electrical insulation and electronic component working voltages.

As an alternative, the electrode 14 can be initially positioned in an intermediate position suitable for shorter needles. Then a longer needle can be sensed by the control 18 when the distal tip of the needle contacts the electrode 14 prior to the electrode 14 being moved to strike an arc. The control 18 can then energize the solenoid 26 (or another unshown solenoid) to move the electrode 14 further away to accommodate the longer needle. If the arc to the proximal portion of the longer needle extinguishes because of the further distance, the control 18 can energize the solenoid 26 to move back to the intermediate position and to then strike a new arc. Additional increments of movement by the electrode 14 can of course be employed to accommodate even a wider range of needle lengths.

The control 18 may include, for example, discrete logic or a microprocessor to perform the required control functions.

The present invention may be readily extended to neutralize not only biohazardous needles but also sharps in general such as sharp-edged surgical instruments like scalpels. Because of the large mass involved, the goal is to dull the cutting edge with an electrical arc rather than trying to destroy the whole blade.

In this case, rather than using an elongate electrode that roughly corresponds to the straight needle, a more localized (e.g., a point source) electrode is mechanically moved not just in one direction, but in two, to follow the contour of the cutting edge. Various edge tracking techniques can be used, but the preferred embodiment employs measuring the arc resistance to provide a measure of the distance between the electrode and the cutting edge. This measurement is then used to control servos that position the electrode. This device can of course also be used to destroy needles.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed:

1. An apparatus for destroying a biohazardous needle having a proximal portion and a distal tip portion, said apparatus comprising:
    an upper electrode adapted to contact said proximal portion, a lower electrode out of contact with the needle spaced therefrom; and
    an electric arc supply connectable between said upper and lower electrodes, said supply being adapted to produce an electric air arc between said lower electrode and said spaced distal tip portion wherein said air arc destroys said needle.

2. An apparatus according to claim 1 wherein said air arc seals said needle.

3. An apparatus according to claim 1, wherein said electric arc supply is adapted to provide said upper electrode with a negative polarity with respect to said lower electrode.

4. An apparatus according to claim 1 further comprising a lower electrode carriage, said carriage being adapted to move said lower electrode into and out of momentary contact with said needle to strike said air arc.

5. An apparatus according to claim 4, wherein said carriage is further adapted to move said lower electrode toward said needle to remove ash therefrom.

6. An apparatus according to claim 4, wherein said carriage is further adapted to move said lower electrode a further distance from said needle if said needle contacts said lower electrode before said lower electrode is moved into momentary contact with said needle.

7. An apparatus according to claim 1 wherein said lower electrode includes an elongate member having a lower portion and an upper portion, said elongate member being adapted to maintain said lower portion closer to said distal tip portion than said upper portion while still spaced therefrom to progressively destroy said needle.

8. A method for destroying a biohazardous needle having a proximal portion and a distal dip portion, said method comprising providing an electric arc supply having an upper and a lower output contact,
    connecting said upper output contact to said proximal portion and said lower output contact spaced from the needle, and creating an air arc between said distal tip portion and said spaced lower output contact, said air arc progressively destroying said needle.

9. A method according to claim 8, further comprising sealing said needle.

10. A method according to claim 8, wherein said upper output contact has a negative polarity with respect to said lower output contact.

11. A method according to claim 8 further comprising moving said lower output contact into and out of momentary contact with said needle to strike said air arc.

12. A method according to claim 8, moving said lower output contact a further distance from said needle if said needle contacts said lower output contact before said lower output contact is moved into momentary contact with said needle.

13. A method according to claim 8, further comprising moving said lower output contact toward said needle to remove ash therefrom.

14. A method according to claim 8 wherein said lower output contact includes an elongate member having a lower portion and an upper portion, said method further comprising maintaining said lower portion closer to said distal tip portion than to said upper portion while still spaced from the needle.

15. An apparatus for neutralizing a biohazardous sharp having a proximal portion and a distal portion, said apparatus comprising a first electrode adapted to contact said proximal portion, a second electrode out of contact with the needle spaced therefrom, and an electric arc supply connectable between said first and second electrodes, said supply being adapted to produce an electric air arc between said second electrode and said spaced distal portion wherein said air arc neutralizes said sharp.

16. A method for neutralizing a biohazardous sharp having a proximal portion and a distal portion, said method comprising providing an electric arc supply having a first and a second output contact, connecting said first output contact to said proximal portion and said second output contact spaced from the needle, and creating an air arc between said distal portion and said spaced second output contact, said air arc neutralizing said sharp.

* * * * *